United States Patent

Metz-Stavenhagen et al.

[11] Patent Number: 6,019,760
[45] Date of Patent: Feb. 1, 2000

[54] SPINE IMPLANT

[75] Inventors: Peter Metz-Stavenhagen, Bad Wildungen; Bernd Robioneck, Preetz, both of Germany

[73] Assignee: Howmedica GmbH, Germany

[21] Appl. No.: 08/782,692

[22] Filed: Jan. 16, 1997

[30] Foreign Application Priority Data

Jan. 19, 1996 [DE] Germany ................ 29600879

[51] Int. Cl.⁷ .................................................. A61B 17/70
[52] U.S. Cl. ............................................. 606/61; 623/17
[58] Field of Search ........................... 606/61, 60, 72, 606/73, 76, 77; 623/17

[56] References Cited

U.S. PATENT DOCUMENTS

| | | | |
|---|---|---|---|
| 4,878,915 | 11/1989 | Brantigen | 623/17 |
| 5,015,247 | 5/1991 | Michelson | 606/61 |
| 5,425,772 | 6/1995 | Brantigen | 623/17 |
| 5,458,638 | 10/1995 | Kuslich et al. | 623/17 |
| 5,489,308 | 2/1996 | Kuslich et al. | 623/17 |
| 5,591,235 | 1/1997 | Kuslich | 623/17 |
| 5,593,409 | 1/1997 | Michelson | 606/61 |
| 5,609,636 | 3/1997 | Kohrs et al. | 623/17 |
| 5,645,598 | 7/1997 | Brosnahan, III | 623/17 |

FOREIGN PATENT DOCUMENTS

| | | |
|---|---|---|
| 0042271 | 12/1981 | European Pat. Off. . |
| 0307241 | 3/1989 | European Pat. Off. . |
| 0461374 | 12/1991 | European Pat. Off. . |
| 0551187 | 7/1993 | European Pat. Off. . |
| 0637440 | 2/1995 | European Pat. Off. . |
| 2642643 | 8/1990 | France . |
| 2710519 | 4/1995 | France . |
| 2716616 | 9/1995 | France . |
| 2649042 | 1/1978 | Germany . |
| 3620549 | 3/1989 | Germany . |
| 4323956 | 10/1994 | Germany . |
| 4416605 | 6/1995 | Germany . |
| 29511146 | 1/1996 | Germany . |
| 2294399 | 5/1996 | United Kingdom . |
| 9514176 | 5/1995 | WIPO . |
| 9526164 | 10/1995 | WIPO . |
| 9628118 | 9/1996 | WIPO . |

*Primary Examiner*—Michael Buiz
*Assistant Examiner*—David O. Reip
*Attorney, Agent, or Firm*—Lerner, David, Littenberg, Krumholz & Mentlik, LLP

[57] ABSTRACT

An intersomatic spine implant is provided which is easily and quickly insertable dorsally into a defective disc. The implant is formed as a hollow body in a substantially cylindrical shape with at least one opening in a side wall for receiving bone material, and the surface of the implant has a roughness which ensures better hold and better conditions for bone ingrowth. In one embodiment, the hollow body can have a self-cutting external thread and can also be either open or closed by means of a cover. In another embodiment, one end of the hollow body comprises a means for turning the body by use of a tool.

2 Claims, 1 Drawing Sheet

SPINE IMPLANT

BACKGROUND OF THE INVENTION

The invention relates to a spine implant.

Intervertebral discs which are damaged generatively or traumatically or which are affected by disease can cause serious physical trouble. Thus, damaged or diseased discs can result in e.g. a reduction of the space between two adjacent vertebrae such that a pressure on the nerves extending within the spine is created and thereby great pains are caused. Significant spinal curvatures can be caused or the motility of two adjacent vertebrae can be strongly limited by a series of diseases, whereby the discs are affected.

For relief of symptoms caused by or related to damaged or diseased discs, it is known to insert implants between adjacent vertebrae in order at least partially to replace the affected discs, whereby the implants have a stabilizing function.

The EP 0 307 241 B1 describes an implant for maintaining a desired space between vertebrae. The implant is inserted in prepared grooves and is roughened on the surface for interlocking with the grooves. Furthermore, the implant has at least one throughgoing slot for receiving bone graft material. The implant, preferably shaped as a square block, is pushed into the grooves by means of a tool which is securely attached to an end of the implant. This has the disadvantage that at first the grooves have to be formed by taking out disc and bone material, and a high precision is necessary to adapt the groove form to the form of the implant so as to achieve an exact and secure positioning of the implant. Especially with a square block implant, it is difficult and takes time to avoid a cant. Corrections during the insertion of the implant must be limited.

An object of this invention is an intersomatic spine implant which is insertable easily and within a relatively short time period.

SUMMARY OF THE INVENTION

The spine implant according to the invention is a hollow body having at least one throughgoing opening in a side wall for receiving bone material. The outer surface of the hollow body has a roughness in order to ensure a better hold and better conditions for bone ingrowth. The hollow body is distinguished in that it has a substantially round cross-section over its entire length.

The implant is to be dorsally inserted into a defective disc parallel to the surface thereof. Thereby, the diameter of the implant is chosen so that the implant reaches into both vertebrae adjacent to the disc above and below in order to allow fixation of the implant by bone ingrowth.

Due to the round cross-sectional form of the implant, for the insertion, a recess can be created by simple drilling in a relatively short period of time. The bore can be of such extent that the implant need only be pushed in. Alternatively, the hollow body can also comprise a self-cutting or self-forming external thread in order that the hollow body can be inserted into the prepared bore (cored hole) by turning. In this case, the thread provides a sufficient hold in the spine.

Especially if the external thread is self-cutting, several throughgoing openings are provided in the side wall of the hollow body, the openings being formed as longitudinal nuts. With the nuts, cutting edges are formed. Bone chips created during insertion are passed into the inside of the hollow body. For insertion, at an end the hollow body can comprise means for turning by using a tool.

An especially favorable shape of the hollow body is a circular-cylindrical shape. At an end opposite to the end which is inserted first, the hollow body can be open and closable with a cover. An advantage of such a closable end is that the hollow body can be filled with spongiose bone material and can subsequently be closed. The cover can be screwable into the open end and can be formed, e.g. as a hexsocket head screw or as a slotted or cross-slotted screw. The hexsocket and the slots in the cover, respectively, can simultaneously together be the means for turning the hollow body upon screwing the hollow body into the spine.

At its dorsally located end, which can be open as described above, the hollow body can be provided with one or several pairs of symmetrically opposed cutouts passing therethrough transversely relative to the longitudinal axis for receiving a rod, and the rod can connect several implants inserted along the spine. Thereby, the inventive implant can also be employed as part of a device for bringing into line and stabilizing, respectively, a damaged section of the spine. Thus, the rod can be employed as a distraction or compression rod.

The cutouts can be holes so that the rod can be pushed subsequently through the implants from the side. If the hollow body is open at its dorsally located end, the cutouts can also be formed like slots extending from the edge of the open end along the longitudinal axis of the hollow body. In this embodiment, the rod can be simultaneously put into all provided implants. At its ventrally located end, the slot-like cutouts can be semi-circular for adaptation to the shape of a round rod.

For fixation of the rod, a screwable cover as described above can be provided, preferably with a portion, of its threaded shank pressing against the rod which is put into the cutouts. Also the rod can have a thread for fixation at the implants. Nuts which engage at both sides of the implants by means of correspondingly formed portions with the holes or the slot-like cutouts fix the implants at the rod. The holes or the semi-circular portions of the slot-like cutouts can be provided with a counterbore, with which collars of the fixing nuts engage.

The hollow body can be closed at the end which is first inserted and can be hemispherical in order to facilitate insertion.

As material for production of the implant, metal is especially suitable, preferably titanium.

In the following some uses for the invention are listed.

In case of intersomatic fusions, the implant can be used without fixation at a rod, and the implant preferably is closable with the described hexsocket head screw. In case of fusions after discitides, also of multi-segmental extension, the implant can be employed in connection with a rod in order to provide sufficient stabilization and above all in order to avoid too strong movements. Such a multi-segmental fixation is also provided for anterior distraction in case of juvenile kyphoses in order to form so-called distraction instruments. Furthermore, the invention can be helpfully applied in case of anterior epiphyseodeses in connection with juvenile scolioses. Also in case of tumors or other lesions, the device according to the invention can be employed at the anterior spine.

DESCRIPTION OF THE PREFERRED EMBODIMENTS

In the following, the invention will be illustrated in more detail with reference to drawings.

DETAILED DESCRIPTION OF THE DRAWINGS

Figure 1A:
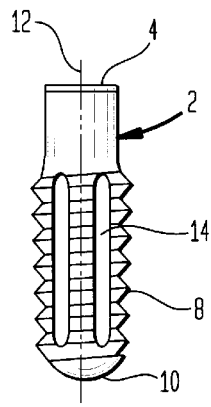
FIG. 1 shows an embodiment of an implant according to the invention in elevational view (in FIGS. 1a and 1b, turned by 90° with respect to each other) and a screwable cover in elevational view (FIG. 1c) and in top plan view (in FIG. 1d), and an implant and cover assembled together with bone material located therein (in FIG. 1e).
Figure 1B:
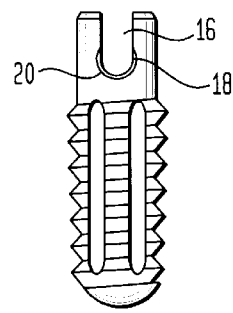
Figure 1C:
Figure 1D:
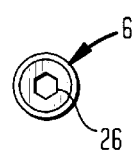

FIG. 1a shows an implant 2 according to the invention which is formed as a hollow body having an open end 4 which is closable with a cover in the form of a hexsocket head screw 6 (shown in FIGS. 1c and 1d). The hollow body of the implant 2 is circular-cylindrical and comprises a self-cutting external thread 8 which extends over the major part of the surface of the implant 2 between the open end 4 and an opposed end 10. Longitudinal throughgoing grooves 14 which are aligned parallel to the longitudinal axis 12 extend in the side wall of the hollow body over the area of the thread 8, whereby the longitudinal grooves form cutting edges for the thread 8. The closed end 10 is formed like a hemisphere.

FIG. 1b shows the implant 2 (also without the hexsocket head screw 6) turned by 90° relative to the representation in FIG. 1a. In this elevational view of the implant 2, two diametrically opposite slot-like cutouts 16 can be seen which extend within an area having no thread from the edge of the open end 4 parallel to the longitudinal axis 12 of the implant. The cutouts 16 are semi-circular at their inwardly directed end 18. The semi-circular portion of the cutouts is radially outside provided with a counterbore 20 for engagement with a nut 22 (see FIG. 2) which is used for fixation of a rod 23 put into the cutout 16, as is illustrated below in more detail.

In FIG. 1c and 1d, a hexsocket head screw 6 is shown, in FIG. 1c in elevational view and in FIG. 1d in top plan view. The screw comprises a thread 24 (shown in FIG. 1c, 1d, 1e and 3) and a hexsocket 26.

Figure 1E:
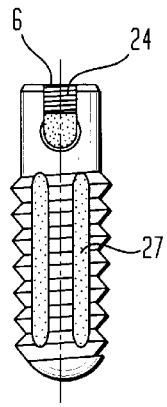

FIG. 1e shows the implant 2 filled with spongial bone material 27 and with the hexsocket head screw 6 screwed on.

The implant 2 is dorsally and in pairs inserted into a defective disc such that both implants lie side-by-side symmetrically with a certain space in the plane of the disc. For that purpose, at first a hole can be bored which has approximately the core diameter of the implant 2, in order to screw this in subsequently. The diameter of the implant is chosen so that the implant upwardly and downwardly extends over the disc into bone material of the adjacent vertebrae in order to achieve a firm anchorage of the implant.

The implant can be screwed in using a screwdriver-like tool, the blade of which is inserted into the cutout 16. Alternatively, the implant can also be screwed in using a hexagonal screwdriver inserted into the hexsocket 26.

Figure 2:
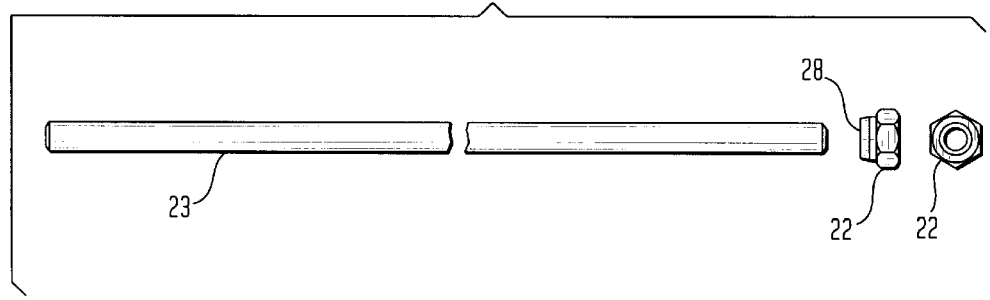
FIG. 2 shows a rod with associated nuts for fixation at the implant of FIG. 1.

FIG. 2 shows an above-mentioned rod 23 which is insertable into the cutout 16 and with which several implants 2 can be connected with each other in order to constitute a device for bringing into line a damaged spine section. The rod 23 can have a thread (not shown) for screwing on nuts 22, of which one is shown in elevational view and in top plan view in FIG. 2. The nuts 22 have a collar 28 the form of which is adapted to the counterbore 20 to engage with the inwardly directed cutout end 18 of the implant 2.

Figure 3:
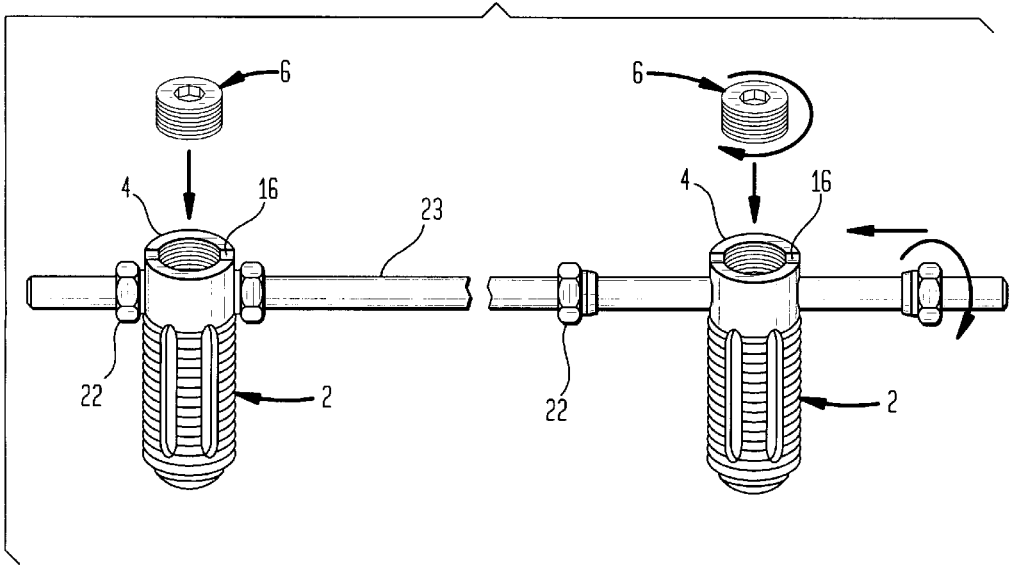
FIG. 3 shows the components of FIGS. 1 and 2 in perspective view as they are assembled as a device for bringing in line a damaged section of the spine.

FIG. 3 shows a device for bringing into line a damaged spine section, the device being composed of components as shown in FIGS. 1 and 2, whereby the same parts are denoted by the same reference numbers.

The device comprises two implants 2 connected by a threaded rod 23 which is put into the cutouts 16 of the two implants. A pair of nuts 22 is provided for each implant for fixation of the rod 23, the nuts being screwed onto the rod 23 and engaging with the inwardly directed ends 18 of the cutouts 16. By means of the hexsocket head screws 6, the open ends 4 of the implants and thus the cutouts can be closed. Therefore, the rod is more or less loosely held on the implants 2. A prefixation can be carried out using the hexsocket head screws 6. The final fixation can be done using the nuts 22. By turning only one nut, the implants can also be put under stress towards each other or away from each other (compressing/distracting).

We claim:

1. A spine implant which is formed as a hollow body (2), said implant comprising a side wall with at least one throughgoing opening (14) for receiving bone material (27) and said implant having a roughened surface, wherein said hollow body (2) has a substantially round cross-section over its entire length, wherein said hollow body has an open end near which is located at least one pair of symmetrically opposed throughgoing cutouts (16) for receiving a rod (23) for connecting several implants, wherein said hollow body has a substantially circular-cylindrical shape, wherein said hollow body comprises a self-cutting or self-forming external thread (8), wherein said open end of said hollow body has a means for turning said body by using a tool, and including also a cover (6) for closing said open end (4), wherein said cutouts (16) are slot-like and are located adjacent to said open end (4), wherein said cutouts have an inwardly directed end (18) and wherein said cutouts are semi-circular at said inwardly directed end (18), and wherein said semi-circular portions of said cutouts (16) have a counterbore (20) for receiving nuts (22) having a collar (28), said nuts fixing a threaded rod (23).

2. An implant according to claim 1 wherein said hollow body has a closed end (10) being curved hemispherically.

* * * * *